United States Patent [19]

Dessau et al.

[11] Patent Number: 5,192,728
[45] Date of Patent: Mar. 9, 1993

[54] TIN-COLATING MICROPOROUS CRYSTALLINE MATERIALS AND THEIR USE AS DEHYDROGENATION, DEHYDROCYCLIZATION REFORMING CATALYSTS

[75] Inventors: Ralph M. Dessau, Edison, N.J.; Ernest W. Valyocsik, Yardley; James C. Vartuli, West Chester, both of Pa.

[73] Assignee: Mobil Oil Corporation, Fairfax, Va.

[21] Appl. No.: 418,377

[22] Filed: Oct. 6, 1989

Related U.S. Application Data

[62] Division of Ser. No. 211,198, Jun. 24, 1988, Pat. No. 4,990,710.

[51] Int. Cl.$^5$ .............................................. B01J 29/30
[52] U.S. Cl. ....................... 502/66; 502/71; 502/74; 502/77
[58] Field of Search ........................ 502/66, 71, 77, 74

[56] References Cited

U.S. PATENT DOCUMENTS

| | | | |
|---|---|---|---|
| Re. 29,948 | 3/1979 | Dwyer et al. ........................ 208/110 |
| 3,702,293 | 11/1972 | Hayes et al. ........................ 208/139 |
| 3,702,294 | 11/1972 | Rausch ................................ 208/139 |
| 3,878,131 | 4/1973 | Hayes ............................ 252/466 PT |
| 4,104,320 | 8/1978 | Bernard et al. .................. 260/673.5 |
| 4,325,808 | 4/1982 | Kim et al. ............................ 208/65 |
| 4,347,394 | 8/1982 | Detz et al. ........................... 585/419 |
| 4,387,258 | 6/1983 | Vadekar et al. .................... 585/259 |
| 4,416,806 | 11/1983 | Bernard et al. ....................... 502/74 |
| 4,418,006 | 11/1983 | Kim et al. ............................. 502/73 |
| 4,435,283 | 3/1984 | Buss et al. ........................... 208/138 |
| 4,456,527 | 6/1984 | Buss et al. ............................. 208/89 |
| 4,486,547 | 12/1984 | Imai et al. ............................. 502/223 |
| 4,487,843 | 12/1984 | Telford et al. .......................... 502/85 |
| 4,487,848 | 12/1984 | Robinson et al. ..................... 502/223 |
| 4,547,472 | 10/1985 | Nordstrand ............................ 502/66 |
| 4,576,805 | 3/1986 | Chang et al. .......................... 423/277 |
| 4,588,495 | 5/1986 | Franck et al. .......................... 208/65 |
| 4,604,371 | 8/1986 | Moorehead ........................... 502/60 |
| 4,614,834 | 9/1986 | Lambert et al. ...................... 585/419 |
| 4,619,906 | 10/1986 | Lambert et al. ....................... 502/66 |

FOREIGN PATENT DOCUMENTS

| | | | |
|---|---|---|---|
| 18488 | 11/1980 | European Pat. Off. ............. 502/77 |
| 0107389 | 4/1984 | European Pat. Off. . |
| 2520636 | 1/1983 | France . |
| 2024790 | 1/1980 | United Kingdom .................. 502/77 |
| 2033358 | 5/1980 | United Kingdom . |
| 2114150 | 8/1983 | United Kingdom . |

OTHER PUBLICATIONS

G. Wengui et al "IR Study of Framework Vibrations and Surface Properties High Silica Zeolites", Zeolites, Elsevir Science, Amsterdam, 1985, p. 279.
Ione, "Structure and Reactivity of Modified Zeolites", Elsevir Science, (1984), pp. 151–155.
Huagong, vol. 15, No. 7 (1986) (with translation).

*Primary Examiner*—Carl F. Dees
*Attorney, Agent, or Firm*—Alexander J. McKillop; Charles J. Speciale; Marina V. Schneller

[57] ABSTRACT

Group VIII metal modified non-acidic tin containing microporous crystalline materials which in catalysis exhibit high selectivity for dehydrogenation and dehydrocyclization are described.

32 Claims, 3 Drawing Sheets a reaction mixture containing no deliberately added aluminum and exhibiting the X-ray diffraction pattern characteristic of ZSM-5 zeolites; in certain examples tin is deliberately added to the silicate synthesis mixture.

TIN-COLATING MICROPOROUS CRYSTALLINE MATERIALS AND THEIR USE AS DEHYDROGENATION, DEHYDROCYCLIZATION REFORMING CATALYSTS

This is a divisional of copending application Ser. No. 211,198, filed on Jun. 24, 1988 and now U.S. Pat. No. 4,990,710, which is relied upon and incorporated by reference herein.

FIELD OF THE INVENTION

Crystalline microporous materials containing a modifier comprising tin are described. The compositions exhibit high selectivity in the catalytic dehydrogenation and/or dehydrocyclization of paraffins. These materials can be employed as reforming catalysts.

BACKGROUND OF THE INVENTION

Naturally occurring and synthetic crystalline microporous materials have been demonstrated to exhibit catalytic properties for various types of hydrocarbon conversions. The term "crystalline" used to refer to these materials relates to the ordered definite crystalline structure of the material which is unique and thus identifiable by a characteristic X-ray diffraction pattern.

The term "microporous" as it refers to such material relates to pores, or channels, with diameters of less than 20 Angstroms. Examples of these microporous crystalline materials include crystalline silicates, crystalline alumino-silicates (zeolites), crystalline ALPOs, crystalline SAPO and related compositions and intercalated pillared materials derived from clays, layered silicates and titanates. The crystalline silicate, alumino silicate (zeolites), ALPOs and SAPOs, have pores of uniform size and channel systems which are uniquely determined by unit structure of the material. The uniform pore size and/or channel systems allow such a material to selectively absorb molecules of certain dimensions and shapes. In the art, microporous material having pores, or channels, of less than 20 Angstroms, can be divided into small, medium and large pore by the diameters of those pores, or channels. The pores of the small pore material have an average diameter of less than 5 Angstroms; medium size pores range from an average diameter of about 5 to about 7 Angstroms, and large pore silicates indicates a diameter of greater than about 7. The word "average" is used to refer to diameter to embrace those species in which the pore is elliptical. Alternatively, the demarcation between small, medium, and large pore materials can be based on the following sorption properties (measured at room temperature for crystallites having a minimum dimenson of 0.1 micron):

1. Small pore: $n-C_6/i-C_6$ sorption ratio greater than approximately 10.
2. Medium pore: $n-C_6/i-C_6$ is less than 10 and $n-C_6$/Mesitylene sorption ratio greater than approximately 5.
3. Large pore: $n-C_6$/Mesitylene sorption ratio less than approximately 5.

In the art, zeolites are a subclass of crystalline microporous silicates. Zeolites can contain aluminum as well as silicon. In some zeolites, the upper limit of the silicon/aluminum atomic ratio is unbounded. ZSM-5 is one such example wherein the silicon/aluminum atomic ratio is at least 2.5 and up to infinity. By way of illustration, U.S. Pat. No. 3,941,871, reissued as U.S. Pat. No. RE 29,948, discloses a porous crystalline silicate made Zeolites can be acidic or non-acidic, depending on the framework aluminum content and on the amount of compensating cations, such as $Na^+$, $K^+$, etc. ALPOs described in U.S. Pat. No. 4,310,440, which is incorporated by reference herein, are neutral. SAPOs described for example in U.S. Pat. No. 4,440,871, which is incorporated by reference herein, can be acidic or non-acidic depending on the ratio of framework Al:P therein and the compensating cation, such as $Na^+$, $K^+$(other than proton species and other than proton forming species such as $NH_4^+$). ELAPOs are described in U.S. Pat. No. 4,500,651, while MeAPOs are described in U.S. Pat. Nos. 4,544,143 and 4,567,029, each of said latter three patents being incorporated by reference herein.

SUMMARY OF THE INVENTION

The present invention is directed to a new composition of matter, to its method of production, and to its use as a catalyst in paraffin dehydrogenation and paraffin dehydrocyclization. The composition comprises a microporous crystalline material containing tin as a modifier. It has been discovered that these tin containing microporous crystalline materials in non-acidic form combined with a dehydrogenation metal exhibit high selectivity for dehydrogenation and/or dehydrocyclization of paraffins. While exhibiting decreased selectivity for hydrogenolysis (especially methane formation) relative to their tin-free counterparts. Furthermore, these compositions are effective reforming catalysts.

DESCRIPTION OF THE DRAWINGS

Each

DETAILED DESCRIPTION OF THE INVENTION

Figure 1A:
FIGS. 1A, 1B and 1C is a scanning electron micrograph of a species of Pt[Sn]-ZSM-5 made in accordance with Examples 1-6.

The tin content of the crystalline microporous materials can range from 0.01 to 20 weight percent. Practically, the tin content will range from 0.1 to 10 weight percent.

The crystalline microporous tin containing materials of the invention are characterized by Si/Al ratios of at least 2. However, the silica:alumina ratio of the zeolite can be up to 1000, or greater. In a preferred embodiment the aluminum content of these materials is less than 0.1 weight percent and more preferably less than 0.02 weight percent.

The crystalline microporous tin containing material of the invention can contain other elements including boron, iron, chromium and gallium. The content of these other elements in the crystalline tin containing silicates can range from 0 to 10 weight percent.

The tin containing crystalline materials of the invention, described herein, are crystalline in the sense that they are identifiable as isostructural with zeolites by X-ray powder diffraction pattern.

The crystalline microporous tin containing material has an X-ray diffraction pattern which corresponds to a zeolite, SAPO, ALPO, etc.

In a preferred embodiment the pore size of the microporous crystalline tin containing silicates ranges from about 5 to about 8 Angstroms. In a preferred embodiment the microporous crystalline material containing tin exhibits the structure of ZSM-5, by X-ray diffraction pattern. The X-ray diffraction pattern of ZSM-5 has been described in U.S. Pat. No. 3,702,886 and RE 29,948 each of which is incorporated by reference herein.

Another aspect of the invention is a catalyst comprising hydrogenation/dehydrogenation metal and the non-acidic crystalline microporous tin containing material. As catalysts these non-acidic forms of compositions exhibit extremely high selectivity for paraffin dehydrogenation and/or dehydrocyclization reactions, under conditions effective for paraffin dehydrogenation and/or aromatization.

The amount of dehydrogenation metal in the catalyst can range from 0.1 to 30 weight percent and preferably 0.01 to 10 weight percent of the crystalline tin containing material. In a preferred embodiment, platinum is the hydrogenation/dehydrogenation metal. However, the hydrogenation/dehydrogenation metal can be any Group VIII metal including those of the platinum group, chromium and vanadium.

The compositions comprising hydrogenation/dehydrogenation metal combined with the crystalline tin containing silicates do not exhibit any appreciable acid activity. These catalysts would meet the criteria of non-acidic catalysts described by Davis and Venuto, J. CATAL. Vol. 15, p. 363 (1969). Thus, a non-equilibrium mixture of xylenes are formed from either n-octane or each individual methylheptane isomer, with the octane yielding more o-xylene and 2-methyl-heptane yielding mostly m-xylene, at conversions between 10 and 60%.

When, as in embodiments herein, the crystalline tin dehydrogenation metal containing material exhibits an X-ray diffraction pattern of a zeolite, at least some of the dehydrogenation metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

Compositions of the invention used in catalysis decrease the hydrogen content of the reactant to produce a product having the same number of carbon atoms as the number of carbon atoms in the reactant. By comparison tin-free counterparts of those compositions catalyzed also hydrogenolysis of paraffins, e.g., to methane, as a major competing side reaction; and, accordingly, the latter compositions exhibit decreased selectivity for the aromatization of paraffins but increased selectivity for $C_1$-$C_5$ paraffin production. Some of the aforementioned catalysts were screened for hexane and heptane aromatization at 538° C. in the presence of nitrogen diluent. The results are shown in Table A below in which the crystalline silicate employed exhibited the diffraction pattern of a ZSM-5.

TABLE A

| Paraffin Aromatixation over Pt ZSM-5 | | | | | |
|---|---|---|---|---|---|
| Support | Paraffin | Conversion | Benz. Sel. | Tol. Sel. | C5-Sel |
| B/ZSM-5 | n-hexane | 52% | 31% | — | 12% (a) |
| " | " | 98% | 51% | 2% | 40% (a) |
| " | heptane | 56% | 56% | 8% | 7% (a) |
| " | " | 95% | 33% | 31% | 34% (a) |
| Ga/ZSM-5 | n-hexane | 37% | 6% | 7% | 66% (b) |
| " | " | 89% | 11% | 10% | 61% (b) |
| " | heptane | 57% | 3% | 12% | 79% (c) |
| " | " | 92% | 4% | 17% | 70% (c) |
| In/ZSM-5 | n-hexane | 60% | 81% | — | 1% |
| " | " | 99+% | 95% | — | 4% |
| " | heptane | 50% | — | 92% | 1% |
| " | " | 99% | — | 97% | 1% |
| Si/ZSM-5 (d) | n-hexane | 58% | 69% | — | 18% (a) |
| " | " | 99% | 72% | — | 26% (a) |
| " | heptane | 34% | 45% | 17% | 14% (a) |
| " | " | 99% | 62% | 4% | 34% (a) |

(a) primarily methane.
(b) mainly propane and propylene.
(c) mainly C3 and C4 olefins.
(d) high silica/alumina ZSM-5.
(e) $H_2$-free selectivity based on carbon The non-acidic platinum catalyst prepared from tin/ZSM-5 provided much higher aromatics selectivity than all the other catalysts examined. Toluene selectivity from heptane was about 85% at 99% conversion ($H_2$ free carbon base).

For comparison purposes, it should be noted that over dual functional platinum on acidic alumina reforming catalysts, the rate of heptane cracking to $C_6^-$ was twice the rate of dehydrocyclization. Cf J. H. Sinfelt, "Bimetallic Catalysts", J. Wiley, New York; p. 141 (1983).

The Pt/Ga-ZSM-5 behaved primarily as dual functional acidic catalyst, leading to severe cracking and formation of $C_3$ and $C_4$ products. Aromatics were only produced in low yields.

The other catalysts, including Pt/B-ZSM-5 and Pt/high silica:alumina ratio as well as those others enumerated in the Table did not show any appreciable acid activity, in that platinum chemistry dominated. Significant metal-catalyzed aromatization was observed; however hydrogenolysis to methane constituted a major competing side reaction. The highest toluene selectivity observed was 50–55%, and in most cases that selectivity was significantly lower. This is in sharp contrast to the aromatic product selectivity of the platinum/tin/ZSM-5. The cause for this difference in platinum behavior from the Pt/tin-ZSM-5 catalyst is not clear.

SYNTHESIS OF THE COMPOSITIONS

One way of incorporating tin into the composition of this invention is by incorporation during the synthesis of the non-acidic crystalline microporous material. Alternatively, tin can be incorporated with the crystalline composition post-synthesis of the microporous crystalline material. The dehydrogenating metal can be incorporated during or after synthesis of the microporous crystalline material. The dehydrogenating metal can be incorporated before, simultaneously with or after tin incorporation.

Alternatively, reverse procedures can be applied in which the dehydrogenation function is first introduced with subsequent tin incorporation. Stepwise preparation includes techniques of cocrystallization, impregnation, or exchange. Cocrystallization can be undertaken in a two phase system described in commonly assigned Ser.

No. 878,555, filed Jun. 26, 1986 and now abandoned. Other elements such as boron, iron chromium, gallium, can also be included. Simultaneous incorporation includes the combination of tin with the dehydrogenation/hydrogenation function during synthesis (i.e., crystallization) or simultaneously after synthesis of the crystalline material.

A tin free material can be treated with tin compounds at elevated temperatures. Such treatments can be conducted so that the source of tin is either in the gaseous or the liquid phase including the aqueous phase (such as tin II). Alternatively, a tin free crystalline reactant can simply be impregnated with tin source and then calcined at temperatures above 400° C.

The tin free reactant can have high silica:alumina ratios or contain other elements such as boron, chronium, iron, and gallium. Reactants and products containing 0.1 weight percent or less aluminum are the preferred embodiments of the examples. In materials of the invention, all cation-exchangeable sites are occupied by non-hydrogen (non-proton) and by non-hydrogen precursors, such as $NH_4^+$. Specifically, such sites are occupied by $Na^+$, $K^+$, $Cs^+$ or admixtures thereof. The alkali metals serve to neutralize any acidity due to framework aluminum. The source of alkali metal cation can derive from cations incorporated during synthesis, in excess of the aluminum content thereof. Alternatively, one can treat the final product with a basic solution of an alkali metal hydroxide as a final step prior to use, as described for example in U.S. Pat. No. 4,652,360.

In a preferred embodiment, the non-acidic crystalline microporous tin containing silicates of the invention are treated with $Pt(NH_3)_4Cl_2$ in aqueous solution which has a pH of at least about 7 to incorporate the necessary platinum for catalyst composition formulation.

The non-acidic, crystalline, microporous, tin modifier and dehydrogenation metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in dehydrogenation and/or dehydrocyclization, the material of the invention will preferably be combined with non-acidic matrix or binder materials. A preferred matrix or binder material would be silica, when the materials of the invention are used in dehydrogenation/hydrogenation or dehydrocyclization. In applications other than hydrogenation, dehydrogenation and/or dehydrocyclization, the matrix or binder material can be any of those including active and inactive material and synthetic or naturally occurring zeolites as well as inorganic materials such as clays, silica and/or metal oxides, e.g. alumina. The latter may be either naturally occurring or in the form of gelatinous precipitates or gels including mixtures of silica and metal oxides. Use of a material in conjunction with the new composition, i.e. combined therewith, which is active, tends to alter the conversion and/or selectivity of the overall catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It may be desirable to provide a catalyst having good crush strength because in commercial use it is desirable to prevent the catalyst from breaking down into powder-like materials. These clay binders have been employed normally only for the purpose of improving the crush strength of the overall catalyst.

Naturally occurring clays which can be composited with the new crystal include the montmorillonite and kaolin families which include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the crystalline tin material can be composited with a porous matrix material such as silica-alumina, silica-magnesia, silica-zirconia, silica-thoria, silica-beryllia, silica-titania we well as ternary compositions such as silica-aluminthoria, silica-alumina-zirconia silica-alumina-magnesia and silica-magnesia-zirconia. The relative proportions of finely divided crystalline material and inorganic oxide gel matrix vary widely, with the crystal content ranging from about 1 to about 90 percent by weight and more usually, particularly when the composite is prepared in the form of beads, in the range of about 2 to about 80 weight percent of the composite.

USE OF THE CATALYST COMPOSITION

These compositions of the invention exhibit high selectivity for dehydrogenation and/or dehydrocyclization and reforming, which is evidenced by the examples. In dehydrogenation, dehydrocyclization and reforming processes, the microporous crystalline tin containing silicates are combined with reforming metals, or dehydrogenation/hydrogenation metals.

CATALYTIC DEHYDROGENATION AND DEHYDROCYCLIZATION

In accordance with the invention catalytic dehydrogenation comprises contacting an aliphatic, with the catalyst composition of the invention produce the corresponding unsaturated analog together with at least one mol of $H_2$. The catalytic dehydrogenation exhibits high selectivity with respect to production of said unsaturated analog, with substantially little, if any, selectivity for hydrogenolysis (cracking) and with substantially little, if any, selectivity for isomerization.

In dehydrogenation the feedstocks comprise at least one unsubstituted or substituted straight or branched chain aliphatic compound in which the aliphatic moiety has two to five carbon atoms. In accordance with the invention, dehydrogenation of the aliphatic moiety occurs to yield the unsaturated analog. When the aliphatic moiety is substituted, the substituents can be aryls substituted or unsubstituted. The class of reactants includes alkanes of 2 to 5 carbon atoms including ethane, propane, butane, isobutane, pentane and 2 methylbutane. Dehydrogenation of those respective alkane reactants will yield ethylene, propylene, butene, isobutene, pentene and isopentene.

The class of reactants includes olefins of 2 to 5 carbon atoms such as ethylene, butane, pentane, and isopentane. Dehydrogenation of ethylene will produce acetylene; dehydrogenation of butene will produce butadiene and dehydrogenation of methyl propene will produce isoprene.

The class of reactants employed in the dehydrogenation of the invention includes aromatic substituted aliphatics, aryl substituted aliphatics. Preferably, the aliphatic group of the aryl substituted aliphatic contains less than four carbon atoms and more preferably more than 1 carbon atom. The aryl substituted aliphatic reactants embrace unsubstituted arylaliphatics and alkyl substituted aryl aliphatics and; similarly, each of the alkyls of said alkyl substituted alkylaryls contains preferably less than 4 carbon atoms. By way of illustration reactants such as ethyl benzene, diethylbenzene, ethyl toluene, and cumene are representative of these compounds. On dehydrogenation in accordance with the invention, ethyl benzene will produce styrene; ethyl toluene will produce p-methylstyrene; cumene, isopropenylbenzene; and diethylbenzene, divinylbenzene.

In accordance with the invention, catalytic dehydrogenation conditions include pressures varying from subatmospheric, to atmospheric to greater than atmospheric. Preferred pressures range from 0.1 atmospheres to atmospheric. However, pressures up to 500 psig can be employed. The dehydrogenation is conducted at elevated temperatures ranging from 400° C. to 700° C. and most preferably from 300° C. to 600° C. Reactor inlet $H_2$/feed ratios are 5 or less; even at reactor inlet ratios of zero (0), there will be a hydrogen partial pressure in the reactor because hydrogen is a bi-product of dehydrogenation. The liquid hourly space velocity of 0.1 to 50, preferably 0.5 to 10.

Under these conditions, the catalytic dehydrogenation of the invention exhibits little if any selectivity for hydrogenolysis or for isomerization. Accordingly, the unsaturated product of the process of the invention can be characterized as substantially free of molecular products of less (fewer number) carbon atoms than the reactants and as substantially free of isomers of the reactant or of isomers of its unsaturated analogs of the reactant.

Dehydrogenation may be conducted in the presence or absence of purposefully added hydrogen and in the presence of diluents inert to conditions of the catalytic dehydrogenation such as nitrogen and methane. In particular, dehydrogenation can be advantageously conducted at low hydrogen pressure.

Dehydrocyclization in accordance with the invention comprises contacting an aliphatic of at least six (6) carbon atoms with the catalytic composition comprising a dehydrogenation/hydrogenation metal which can be any Group VIII metal, preferably platinum.

The feedstocks charge to the new reforming process can be straight-run, thermal, or hydrocracker naphtha. Preferably, for high increases in the aromatic content and high octane numbers of the reformate, the charge to the reformer is a naphtha rich in $C_6$ and $C_7$ paraffins; these are generally difficult to reform selectively using conventional catalysts (such as chlorided Pt-alumina). Naphthas can be obtained by separating the charge into two fractions: a light naphtha and a heavy naphtha. Conventionally such separation is by distillation. The boiling range of the light naphtha is from about 80° F. to about 400° F. and the boiling range of the heavy naphtha will be from up to about 650° F. The light naphtha will be rich in $C_6$-$C_{10}$ paraffins, and specifically $C_6$ and $C_7$ paraffins. In accordance with one embodiment when the light naphtha is reformed in accordance with the invention, the heavy naphtha will be processed by conventional reforming. The naphtha fractions may be hydrotreated prior to reforming; but hydrotreating is not necessarily required when using the catalyst in accordance with the invention, as the catalyst described below does not appear to be deactivated by, e.g., sulfur. Initial hydrotreating of a hydrocarbon feed serves to convert sulfur, nitrogen and oxygen derivatives of hydrocarbon to hydrogen sulfide, ammonia, and water while depositing metal contaminant from hydrodecomposition of any organo-metal compounds. Where desired, interstage processing of the effluent from the hydrotreating zone may be effected. Such interstage processing may be undertaken, for example, to provide additional hydrogen, to add or remove heat or to withdraw a portion of the hydrotreated stream for treatment which need not be reformed. Hydrotreating of the heavy naphta fraction may be essential, prior to reforming in a conventional reforming process. Suitably, the temperature in the hydrotreating catalyst bed will be within the approximate range of 550° F. to 850° F. The feed is conducted through the bed at an overall space velocity between about 0.1 and about 10 and preferably between 0.2 and about 2, with hydrogen initially present in the hydrotreating zone in an amount between about 1000 and 10,000 standard cubic feet per barrel of feed, corresponding to a ratio of between about 2.4 and about 24 moles of hydrogen per mole of hydrocarbon. The catalyst may be any of the known hydrotreating catalysts, many of which are available as staple articles of commerce. These hydrotreating catalysts are generally metals or metal oxides of Group VIB and/or Group VIII deposited on a solid porous support, such as silica and/or metal oxides such as alumina, titania, zirconia or mixtures thereof. Representative Group VIB metals include molybdenum, chromium and tungsten and Group VIII metals include nickel, cobalt, palladium and platinum. These metal components are deposited, in the form of metals or metal oxides, on the indicated supports in amounts generally between about 0.1 and about 20 weight percent. One particularly useful hydrotreating catalyst is a commercial catalyst known as Chevron ICR 106 which is a nickel-tungsten-alumina-silica-titania catalyst.

When dehydrogenation, dehydrocyclization or reforming is undertaken over the catalyst in accordance with the invention, the temperature can range broadly from 800° F. to 1100° F., generally being greater than about 900° F., preferably being 900° F. (482° C.) to 1050° F.; the pressure will be from about 1 atmosphere to 500 psig, preferably from 30 psig to 250 psig; inlet $H_2$/hydrocarbon can be 5 or less, even zero (0) (because of hydrogen production during reforming, there will be a hydrogen partial pressure in the unit); while the LHSV (liquid hourly space velocity) can be 0.1 to 20, preferably 0.1 to 10.

Reforming of the heavy naphtha fraction, boiling range of up to 650° F. can be undertaken separately from the light naphtha fraction, by conventional reforming. Conventional reforming may be semi-regenerative, cyclic or continuous. Process conditions in reforming include pressures of about 0 to 500 psig, preferably, the pressures used herein range from 0–250 psig and most preferably are 0–100 psig; temperatures of 800° to 1100° F.; $H_2$/HC molar ratios of 0 to 20:1 preferably of about 2:1 to about 6:1; LHSV of 0.1 to 20 $hr^{-1}$.

Conventional reforming catalysts for this stage can include conventional reforming hydrogenation/dehydrogenation metals on aluminas. Those reforming hydrogenation/dehydrogenation metals include: platinum, platinum-rhenium; platinum with iridium, rhenium, rhodium or admixtures thereof; or platinum/tin. These hydrogenation/dehydrogenation metal combinations are on alumina and are chlorided; generally they are presulfided prior to use on feeds containing less than about 1 ppm sulfur.

Selectivity and aging characteristics at low hydrogen partial pressures may be superior to conventional non-zeolitic reforming catalysts. With these catalysts, the reforming process can be run in the absence of added hydrogen, and preferably even, in the presence of diluents such as nitrogen, methane, propane, pentanes, and $C_6-C_8$ aromatics.

EXAMPLES

EXAMPLE 1

Tin ZSM-5 silicate was synthesized in a static system at 300° F. 400 g 28.5% sodium silicate (Q-brand) was added to a solution of 60 g 50% tetramethylammonium chloride, 15 g $SnCl_4.5H_2O$, 30 g 98% $H_2SO_4$, and 60 g TPA+Br- in 2250 g water. The mixture was stirred and then placed in a polypropylene bottle in an autoclave for 5 days. The product was 85% crystalline ZSM-5 and consisted of large 5-10 micron crystals. In this and following preparations the zeolitic silicates produced were characterized as having at least one crystal dimension which was at least 0.5 microns; it analyzed for 80.4% $SiO_2$, 0.30% $Al_2O_3$, 3.78% Sn, 2.00% Na, 7.70% C, and 1.05% N.

EXAMPLE 2

Another tin containing ZSM-5 sample was synthesized by dissolving 0.69 g $Sn(II)SO_4$ in 170 g de-ionized water and then adding 3.39 g NaOH. To this was added 6.38 g tetrapropylammonium bromide. The mixture was transferred to a 300 ml stainless steel autoclave and 16.0 g of a low aluminum content silica gel (SPEX Ind.) was added with stirring. The hydrogel formed by this reaction mixture is described by the following mole ratios:

| $SiO_2$/Sn | $H_2O$/Sn | $OH-/SiO_2$ | $Na+/SiO_2$ | $TPA+/SiC_2$ |
|---|---|---|---|---|
| 75 | 40 | 0.30 | 0.35 | 0.10 |

The hydrogel was reacted at 160° C. for 5 days with stirring (400 rpm) before quenching. The resulting crystalline product was processed in the usual manner by filtering, washing, and drying. X-ray diffraction analysis of the product zeolite showed it to be 100% crystalline ZSM-5. SEM indicated an average crystal size greater than 2 microns.

EXAMPLE 3

A tin containing ZSM-5 sample was synthesized in a similar manner except that the $SiO_2$/Sn ratio was 150 and the $Na+/SiO_2$ was 0.31. The crystalline ZSM-5 product contained 1.36% Sn, 0.0025% Al, 0.93% Na, and 89.31% Ash.

EXAMPLE 4

A tin containing ZSM-5 sample was synthesized in a similar manner except that the $SiO_2$/Sn ratio was 50, the $Na+/SiO_2$ was 0.38, and the synthesis time was 4 days.

EXAMPLE 5

A tin containing ZSM-5 sample was synthesized at a $SiO_2$/Sn ratio of 38, a $Na+/SiO_2$ ratio of 0.40, and a synthesis time of 3 days.

Figure 1B:
Figure 1C:
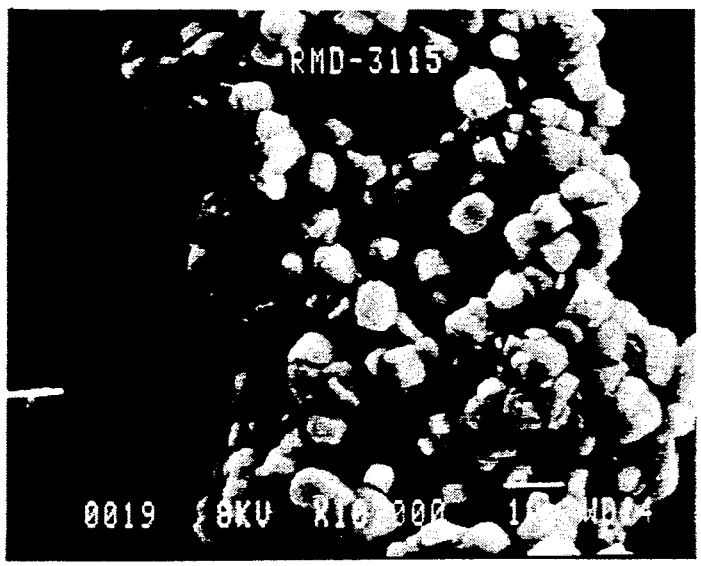

Tin incorporation was achieved during the zeolite synthesis, i.e., tin salts were added directly to the high silica ZSM-5 synthesis mixture. SEM data suggests that a significant portion of the tin is located outside of the large crystals formed (FIG. 1). Nevertheless, some tin must be inside the ZSM-5 crystals, since it modifies the selectivity of the platinum, which itself is intracrystalline.

Platinum was incorporated by ion-exchange of the calcined zeolites, probably, via exchange for sodium ions associated with internal silyloxy groups. The presence of intracrystalline (intrazeolitic) platinum was confirmed by the extremely low benzene hydrogenation rates (TON=4 $min^{-1}$ at 100° C.) measured for these catalysts.

EXAMPLE 6

Platinum incorporation into the silicates of Examples 1-5 was undertaken. The as-synthesized tin silicates were calcined first in nitrogen and then in air at 520° C. The calcined materials were ion-exchanged with aqueous $Pt(NH_3)_4Cl_2$ at room temperature; typically, 15-20 mg per gram silicate was used in a non-acidic aqueous medium. The platinum tetramine-containing silicates were then calcined in oxygen to 350° C. at 0.5° C./min.

Elemental analysis of the tin silicate of Example 3 after platinum incorporation indicated Pt=0.80%, Sn=1.54%, Al=31 ppm.

Elemental analysis of the tin silicate of Example 1 after platinum incorporation, Pt=0.65%, Sn=3.50%, Al=0.093%.

EXAMPLE 7

A solution of 11.3 g $SnCl_2-H_2O$ in 100 ml methanol was formed. To that solution was added 20 g of a sample of H-ZSM-5 (silica:alumina ratio of 70:1). Then 2.5 ml of an aqueous solution of $H_2PtCl_6$ (1.3 g) was also added to the solution. The mixture was allowed to stand for 4 hours. The product was decanted, washed with 10×100 ml 3A denatured alcohol and let stand overnight under 100 ml 3-A. [3-A refers to a dessicant by Linde]. The product was decanted, washed with 100 ml 3-A and dried in an oven at 100° C.

The composition of Example 7 is inter alia acidic and thus not a part of our invention. The composition of Example 7 exhibits different properties from the non-acidic platinum tin-ZSM-5 of the invention as shown below:

|  | Non-Acidic Catalyst of the Invention | Acidic Composition of Ex. 7 |
|---|---|---|
| α value in He 1 hr on stream | 424 | 62 |
| Benzene selectivity from α value test | 50.4 | 2.0 |

The composition in accordance with the invention was compared against the composition of Example 7. Hexane was the feed; and the numerical value, referred to as α in the foregoing table, is used as a measure of the hexane conversion activity. From the foregoing results it can be noted that the composition in accordance with the invention exhibits greater hexane conversion activity than the Example 7 composition and in the α value test the catalyst of the invention exhibited greater selectivity for hexane conversion to benzene.

The hydrogen consumption of the Example 7 product [at 950° F., 150 psig, 2.5 WHSV (hydrogen:feed:=5, wherein the feed was 25 methylcyclopentane +75 n-$C_7$)] far exceeded that minimal hydrogen consumption of the composition of the invention. However, the Example 7 acidic product appeared to age less rapidly than the non-acidic composition.

EXAMPLE 8

The ability of some catalysts of Examples 1–6 to aromatize n-heptane to toluene was assessed at 538° C. and 30 torr heptane in nitrogen. Heptane was introduced into the reactor in a nitrogen stream passing through a vaporizer containing heptane at 15°–20° C. The presence of tin in these Pt/ZSM-5 catalysts greatly increased the toluene yield and suppressed the amount of methane formed. Some of the data obtained is shown below; scandium, titanium, and boron-containing Pt/ZSM-5 catalysts, prepared in a similar manner, are included for comparison purposes. Yields shown are on a hydrogen-free weight basis.

| Catalyst | SnZSM-5 Source | Conver. | $CH_4$ Yld. | Toluene Yld. | Tol. Sel. |
|---|---|---|---|---|---|
| Pt/SnZSM-5 | Ex. 3 | 91.7% | 6.5% | 63.0% | 57.8% |
| Pt/SnZSM-5 | Ex. 1 | 95.1% | 1.5% | 82.3% | 86.5% |
| Pt/SnZSM-5 | Ex. 2 | 97.7% | 0.3% | 95.4% | 97.7% |
| Pt/SnZSM-5 | Ex. 4 | 99.7% | 0.6% | 94.5% | 94.8% |
| Pt/SnZSM-5 | Ex. 5 | 98.4% | 0.2% | 96.4% | 98.1% |
| Pt/ScZSM-5 | | 96.3% | 15.4% | 37.5% | 38.9% |
| Pt/TiZSM-5 | | 96.1% | 18.9% | 30.6% | 31.8% |
| Pt/B-ZSM-5 | | 94.7% | 19.6% | 28.6% | 30.2% |

EXAMPLE 9

The reforming of a hydrotreated Arab light naphtha, b.p. 180°–250° F., was studied at 1000° F. in nitrogen. The results are shown below:

| Catalyst | | Pt/Sn-ZSM-5 | Pt/Sn-ZSM-5 |
|---|---|---|---|
| SnZSM-5 Source | | Ex. 2 | Ex. 5 |
| Temperature | | 1000° F. | 1000° F. |
| Pressure | | atm. | atm. |
| WHSV | | 4.0 | 2.0 |
| $N_2$/HC | | 3 | 4 |
| | Feed Composition | Product ($H_2$-free* weight basis) | |
| $C_1$–$C_4$ | 0 | 0.74% | 0.69% |
| 2MC5 | 9.35% | 5.75% | 5.31% |
| 3MC5 | 7.11% | 4.32% | 3.88% |
| n-C6 | 24.22% | 3.27% | 5.13% |
| BENZENE | 2.12% | 24.35% | 24.83% |
| 2MC6 | 8.41% | 5.24% | 4.69% |
| 3MC6 | 7.22% | 3.90% | 3.52% |
| n-C7 | 17.05% | 1.21% | 3.17% |
| TOLUENE | 3.23% | 21.62% | 24.21% |

*Determined by on-line Gas chromatography on a 30 m DB-1 column.

Selective conversion of the normal paraffins to aromatics was observed.

EXAMPLE 10

Figure 2:
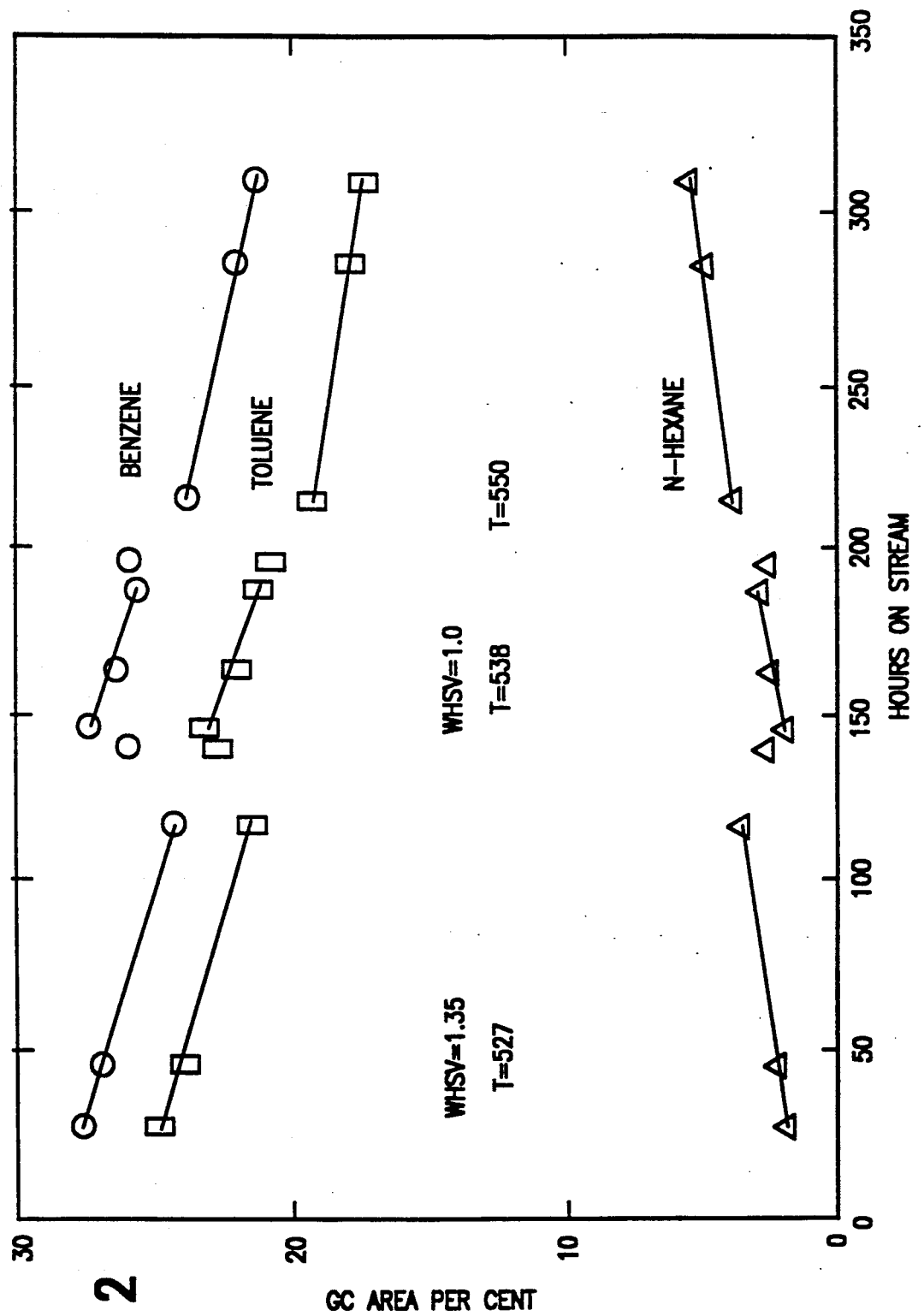
FIG. 2 is a graph of gas chromatography analysis of benzene and toluene (GC area per cent) production vs. hours on stream.

An extended light naphtha reforming run was conducted over a 0.9% Pt/Sn-ZSM-5 catalyst of Example 2 as shown in FIG. 2. The initial inlet temperature was 527° C., and this was increased incrementally to 550° C. WHSV was 1.35 initially, and later, 1.0. The on-line GC yields of both benzene and toluene are shown in FIG. 2. Formation of $C_1$–$C_4$ light gases was quite low: at 45 hours on stream light gas formed was about 0.6%, and about 1.5% at 300 hours on stream.

Figure 3:
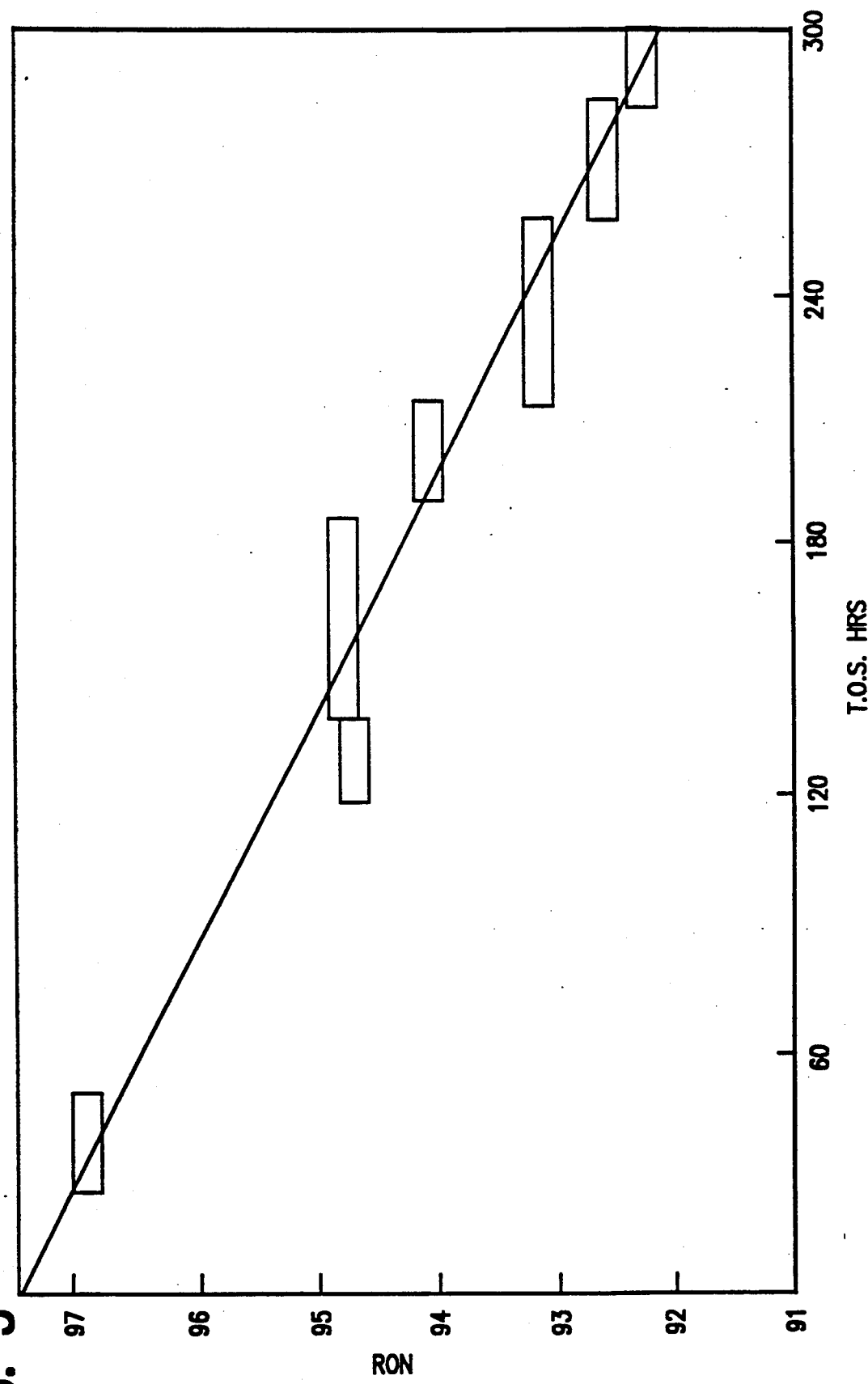
FIG. 3 is a plot of RON of liquid products vs. time on stream.

Througout the run, the liquid product was collected in a $CaCl_2$-ice bath at approximately −40° C. Overall liquid recovery was 90–92 weight per cent of feed. The measured research octane ratings (RON+0) of the various fractions collected are shown in FIG. 3. The RON values ranged from 97 after 1 day on stream to better than 92 after 12 days. The aging rate was less than ½ an octane number per day. The liquid products contained significant amounts of olefins as indicated by their bromine numbers which ranged from 44 to 33.

The very high aromatization selectives of these platinum/tin ZSM-5 catalysts, and their apparent stability in the absence of added hydrogen, make them ideal candidates for reforming catalysts.

What is claimed is:

1. A non-acidic catalyst composition consisting essentially of
   dehydrogenation metal and a non-acidic microporous crystalline material containing tin.

2. The catalyst composition of claim 1, wherein the amount of said metal ranges from 0.1 to 20 weight percent.

3. The catalyst composition of claim 1 wherein the amount of tin ranges from 0.1 to 20 weight percent.

4. The catalyst composition of claim 1 wherein the material exhibits an X-ray diffraction pattern of a zeolite.

5. The catalyst composition of claim 1, wherein the dehydrogenation metal is a Group VIII metal.

6. The catalyst composition of claim 1, wherein the dehydrogenation metal is platinum.

7. The catalyst composition of claim 6, wherein the platinum is intrazeolitic.

8. The catalyst composition of claim 1, wherein tin incorporation into said material is as a Sn(II) salt.

9. The catalyst composition of claim 8, wherein the salt is a sulfate.

10. The catalyst composition of claim 7, wherein at least some of said tin is intrazeolitic.

11. The catalyst composition of claim 1 wherein the non-acidic microporous crystalline tin containing material is the reaction product of a source of silica and a Sn(II) salt.

12. The catalyst composition of claim 4, wherein the non-acidic microporous crystalline tin containing material is the reaction product of a source of silica and a Sn(II) salt.

13. The catalyst composition of claim 6, wherein platinum is exchanged on said material in a non-acidic medium.

14. The catalyst composition of claim 1, wherein the material is isostructural with a zeolite and contains cations of alkali metal or alkali earth metal in excess of the aluminum content of the zeolite.

15. The catalyst composition of claim 1, wherein the material is a silicate.

16. The catalyst composition of claim 1, wherein the material contains less than 0.1 weight percent aluminum.

17. The catalyst composition of claim 13, wherein the material contains less than 0.1 weight percent aluminum.

18. The catalyst composition of claim 12, wherein the material contains less than 0.1 weight percent aluminum.

19. In a catalyst comprising a dehydrogenation/hydrogenation metal and a support, the improvement wherein said support consists essentially of a tin containing non-acidic microporous crystalline material, containing 0.1 to 20 weight percent tin, the crystals of which have at least one dimension which is greater than 0.5 microns.

20. The crystalline material of claim 17 wherein the weight percent of tin ranges up to 10 weight percent.

21. The catalyst composition of claim 1 wherein the dehydrogenation/hydrogenation metal is combined with said non-acidic microporous crystalline material under non-acidic conditions.

22. The catalyst composition of claim 1, wherein the microporous crystalline material exhibits the X-ray diffraction pattern of ZSM-5.

23. The catalyst composition of claim 2, wherein the microporous crystalline material exhibits the X-ray diffraction pattern of ZSM-5.

24. The catalyst composition of claim 3, wherein the microporous crystalline material exhibits the X-ray diffraction pattern of ZSM-5.

25. The catalyst composition of claim 4, wherein the microporous crystalline material exhibits the X-ray diffraction pattern of ZSM-5.

26. The catalyst composition of claim 5, wherein the microporous crystalline material exhibits the X-ray diffraction pattern of ZSM-5.

27. The catalyst composition of claim 6, wherein the microporous crystalline material exhibits the X-ray diffraction pattern of ZSM-5.

28. The catalyst composition of claim 7, wherein the microporous crystalline material exhibits the X-ray diffraction pattern of ZSM-5.

29. The catalyst composition of claim 10, wherein the microporous crystalline material exhibits the X-ray diffraction pattern of ZSM-5.

30. The catalyst composition of claim 28, wherein the platinum comprises 0.1 to 20 weight percent of the catalyst composition.

31. The catalyst composition of claim 30, wherein the tin comprises 0.1 to 20 weight percent of the catalyst composition.

32. The catalyst of claim 19, wherein the microporous crystalline material exhibits an X-ray diffraction pattern of ZSM-5.

* * * * *